(12) United States Patent
Edwards et al.

(10) Patent No.: US 8,302,605 B2
(45) Date of Patent: Nov. 6, 2012

(54) MASK ASSEMBLY, AND FRAME AND SWIVEL CONNECTOR THEREFOR

(75) Inventors: Craig David Edwards, Annandale (AU); Lemmy Nga, Glenwood (AU); Michiel Kooij, Amsterdam (NL); Luke Maguire, Stanmore (AU)

(73) Assignee: ResMed Limited, Bella Vista (AU)

( * ) Notice: Subject to any disclaimer, the term of this patent is extended or adjusted under 35 U.S.C. 154(b) by 746 days.

(21) Appl. No.: 12/312,549

(22) PCT Filed: Nov. 15, 2007

(86) PCT No.: PCT/AU2007/001758
§ 371 (c)(1),
(2), (4) Date: May 15, 2009

(87) PCT Pub. No.: WO2008/058338
PCT Pub. Date: May 22, 2008

(65) Prior Publication Data
US 2010/0000538 A1    Jan. 7, 2010

Related U.S. Application Data

(60) Provisional application No. 60/929,821, filed on Jul. 13, 2007.

(30) Foreign Application Priority Data

Nov. 17, 2006  (AU) ................. 2006906405

(51) Int. Cl.
*A61M 16/06*  (2006.01)
*A62B 18/02*  (2006.01)

(52) U.S. Cl. ................. 128/206.24; 128/206.21
(58) Field of Classification Search ............ 128/202.27, 128/205.24, 206.24, 200.24, 205.25
See application file for complete search history.

(56) References Cited

U.S. PATENT DOCUMENTS

| | | | | |
|---|---|---|---|---|
| 1,176,886 | A | * | 3/1916 | Dickeens ................. 128/207.13 |
| 4,274,406 | A | | 6/1981 | Bartholomew |
| 4,907,584 | A | * | 3/1990 | McGinnis ................. 128/206.24 |
| 4,971,051 | A | * | 11/1990 | Toffolon ................. 128/206.26 |
| D333,015 | S | * | 2/1993 | Farmer et al. ............. D24/110.4 |
| 5,647,357 | A | * | 7/1997 | Barnett et al. ........... 128/206.24 |
| 5,746,201 | A | * | 5/1998 | Kidd ........................ 128/206.24 |

(Continued)

FOREIGN PATENT DOCUMENTS
EP    1027905    6/2005
(Continued)

OTHER PUBLICATIONS

International Search Report for PCT/AU2007/001758, dated Jan. 31, 2008.

*Primary Examiner* — Stephen Crow
(74) *Attorney, Agent, or Firm* — Nixon & Vanderhye P.C.

(57) ABSTRACT

A mask assembly for use in providing a supply of air at positive pressure to the airways of a patient includes a frame and an elbow. The elbow is rotatable with respect to the frame when assembled. The frame includes an elbow-receiving portion. The elbow and elbow-receiving portion of the frame are adapted to include respective interlocking sealing portions and one of the elbow and elbow-receiving portion includes a flexible element that upon assembly flexes to introduce a preload that effects a seal between the respective interlocking sealing portions.

22 Claims, 18 Drawing Sheets

U.S. PATENT DOCUMENTS

| | | | | |
|---|---|---|---|---|
| 5,884,624 A * | 3/1999 | Barnett et al. | ............ | 128/206.24 |
| 5,921,239 A * | 7/1999 | McCall et al. | ............ | 128/205.25 |
| 6,039,044 A * | 3/2000 | Sullivan | ................... | 128/205.25 |
| 6,192,886 B1 * | 2/2001 | Rudolph | ................... | 128/207.13 |
| 6,397,847 B1 * | 6/2002 | Scarberry et al. | ........ | 128/206.24 |
| 6,412,487 B1 * | 7/2002 | Gunaratnam et al. | ... | 128/206.24 |
| 6,418,928 B1 * | 7/2002 | Bordewick et al. | ...... | 128/205.25 |
| 6,431,172 B1 * | 8/2002 | Bordewick | ............... | 128/207.18 |
| 6,467,483 B1 * | 10/2002 | Kopacko et al. | ......... | 128/207.12 |
| 6,491,034 B1 * | 12/2002 | Gunaratnam et al. | ... | 128/204.18 |
| 6,532,961 B1 * | 3/2003 | Kwok et al. | ............. | 128/206.21 |
| 6,595,214 B1 * | 7/2003 | Hecker et al. | ............ | 128/207.13 |
| 6,615,830 B1 | 9/2003 | Serowski et al. | | |
| 6,631,718 B1 * | 10/2003 | Lovell | ...................... | 128/206.24 |
| 6,851,425 B2 * | 2/2005 | Jaffre et al. | .............. | 128/204.18 |
| 6,851,428 B2 * | 2/2005 | Dennis | .................... | 128/205.25 |
| 2003/0221691 A1 * | 12/2003 | Biener et al. | ............. | 128/206.24 |
| 2004/0112383 A1 * | 6/2004 | Curti et al. | ............... | 128/204.18 |
| 2004/0144386 A1 * | 7/2004 | Frater et al. | .............. | 128/206.24 |
| 2006/0081250 A1 * | 4/2006 | Bordewick et al. | ...... | 128/206.11 |
| 2007/0137653 A1 * | 6/2007 | Wood | ....................... | 128/207.18 |

FOREIGN PATENT DOCUMENTS

| WO | WO 2005/063326 | 7/2005 |
|---|---|---|
| WO | WO 2006/133480 | 12/2006 |

* cited by examiner

MASK ASSEMBLY, AND FRAME AND SWIVEL CONNECTOR THEREFOR

CROSS-REFERENCE TO RELATED APPLICATION

This application is the U.S. national phase of International Application No. PCT/AU2007/001758, filed Nov. 15, 2007, which designated the U.S. and claims the benefit of Australian Provisional Patent Application No. AU 2006906405, filed Nov. 17, 2006, and U.S. Provisional Patent Application No. 60/929,821, filed Jul. 13, 2007, each of which is incorporated herein by reference in its entirety.

Also, WO 2004/022147, filed Sep. 5, 2003, is incorporated herein by reference in its entirety.

FIELD OF THE INVENTION

The present invention relates generally to a sealing arrangement and more particularly to a mask assembly (also referred to as a mask) and a mask frame and a mask swivel connector therefore and the formation of a seal between the mask swivel connector (e.g., mask elbow) and the mask frame.

Aspects of the invention have been developed primarily for use with ventilator masks and will be described hereinafter with reference to this application. However, it should be appreciated that aspects of the invention are not limited to this particular field of use and could also be used in the context of masks for CPAP systems, bi-level systems, or any other system or mask associated with respiratory therapy. In embodiments, the mask may be modified to include a vent.

BACKGROUND OF THE INVENTION

Difficulties in creating a mask that provides a seal between the frame and the swivel connector or elbow have been experienced in the art for some time.

One aim is to make a seal that achieves minimal leak over the tolerance range expected from the manufacturing process of the elbow and frame. In many prior art masks, this seal is attempted by controlling the tolerances associated with the elbow and frame very closely to provide a minimum clearance between the elbow and frame while still allowing rotation. It has been found that it is difficult to control leak at tolerance limits in these designs.

For any material having tolerances that are harder to control, the problem of achieving a suitably low clearance for sealing between the elbow and frame is exacerbated. Polypropylene is one example. Parts made of polypropylene must be dimensioned with larger tolerances because this material is harder to mold to precise dimensions. Therefore, minimizing leak at tolerance limits in a controlled clearance type seal with polypropylene parts is very difficult.

Another aim is to reduce friction when the swivel connector or elbow is rotated. However, a small amount of friction is considered advantageous. This has been a difficult balance to achieve to date.

Another aim is to provide a sealing arrangement that does not substantially increase the cost of goods.

SUMMARY OF THE INVENTION

According to an aspect of the invention, a mask assembly is provided for use in supplying air at positive pressure to the airways of a patient. The mask assembly includes a frame and an elbow. The elbow is rotatable with respect to the frame when assembled. The frame includes an elbow-receiving portion. The elbow and elbow-receiving portion of the frame are adapted to include respective interlocking sealing portions and one of the elbow and elbow-receiving portion includes a flexible element that upon assembly flexes to introduce a preload that effects a seal between the respective interlocking sealing portions.

In an embodiment, the flexible element may reside on the elbow-receiving portion of the frame.

In an embodiment, the elbow-receiving portion of the frame may be constructed from polypropylene.

In an embodiment, the elbow may be constructed from polycarbonate.

According to another aspect of the invention, a method for assembling a mask frame and elbow is provided. The method includes inserting a male portion of the elbow into a female portion of the frame until a circumferential flange of the male portion abuts at least one rib on an outer face of the frame, supporting an inside surface of the frame adjacent the flange in use, and pressing the male portion into the female portion such that an interlocking portion of the female portion moves into register with a cooperating portion of the male portion, and the at least one rib is biased against the flange such that the interlocking portion is held in register with the co-operating portion.

In an embodiment, the flange may be annular.

In an embodiment, the at least one rib may be a circumferential rib positioned concentrically with the aperture.

In an embodiment, the interlocking portion may include a circumferential rib and the co-operating portion may include a circumferential groove adapted to receive at least a portion of the rib.

According to another aspect of the invention, a frame is provided for use in a mask assembly used in respiratory therapies. The mask assembly is connectable to an air delivery conduit via a swivel connector and in use has an interior and an exterior. The frame includes a swivel connector-receiving portion. The swivel connector-receiving portion includes a flexing portion and an interlocking portion. The interlocking portion is adapted to engage with a corresponding interlocking portion on the swivel connector and the flexing portion is adapted to flex upon engagement with the swivel connector and to thereby induce a seal between the respective interlocking portions to substantially reduce a leak flow of air from a mask assembly interior to a mask assembly exterior between the frame and swivel connector in use.

In an embodiment, the swivel connector-receiving portion may be a swivel elbow-receiving portion.

In an embodiment, the flexing portion may be constructed from polypropylene.

In an embodiment, the swivel connector receiving portion may be a substantially cylindrical portion having an inside diameter, a proximal end, and a distal end.

In an embodiment, the swivel connector receiving portion may include an interlocking portion near the distal end.

In an embodiment, the interlocking portion may be located on an interior surface of the swivel connector receiving portion.

In an embodiment, the frame may define a length between the proximal end and the interlocking portion.

In an embodiment, the swivel connector receiving portion is adapted for engagement with a swivel connector having a substantially cylindrical portion having an external diameter and a length.

In an embodiment, the inside diameter of the substantially cylindrical portion of the frame is substantially larger than the external diameter of the substantially cylindrical portion of the swivel connector.

In an embodiment, the length of the cylindrical portion of the swivel connector-receiving portion of the frame is less than the length of the cylindrical portion of the swivel connector.

According to another aspect of the invention, a connector is provided and is adapted to sealingly and swivelingly interconnect an air delivery conduit and a frame of a mask assembly for use in non-invasive ventilation. The connector includes a first end for interconnection with the air delivery conduit and a second end for interconnection with the frame. The second end has an interlocking portion adapted to swivelingly engage with a corresponding interlocking portion of the frame and upon flexure of a flexing portion of the frame to sealingly engage thereto.

In an embodiment, the connector may be a swivel elbow.

In an embodiment, the connector may be constructed from polycarbonate.

According to another aspect of the invention, an assembly including a frame and a connector may be provided.

Another aspect of the invention relates to a mask assembly including a frame including a front surface and a tube portion protruding from the front surface rearwards into an internal volume of the frame, and a connector provided to the frame and adapted to be connected to an air delivery tube that delivers breathable gas to the patient. The connector includes a tubular insertion portion adapted to be received in the tube portion. The tube portion includes an inwardly facing circumferential rib that is adapted to interlock with a circumferential groove provided on an outer surface of the insertion portion.

Another aspect of the invention relates to a mask assembly including a frame and a connector provided to the frame and adapted to be connected to an air delivery tube that delivers breathable gas to the patient. The connector is engaged with the frame to allow controlled rotation of the connector with respect to the frame due to friction between the connector and frame.

Other aspects, features, and advantages of this invention will become apparent from the following detailed description when taken in conjunction with the accompanying drawings, which are a part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Figure 1:
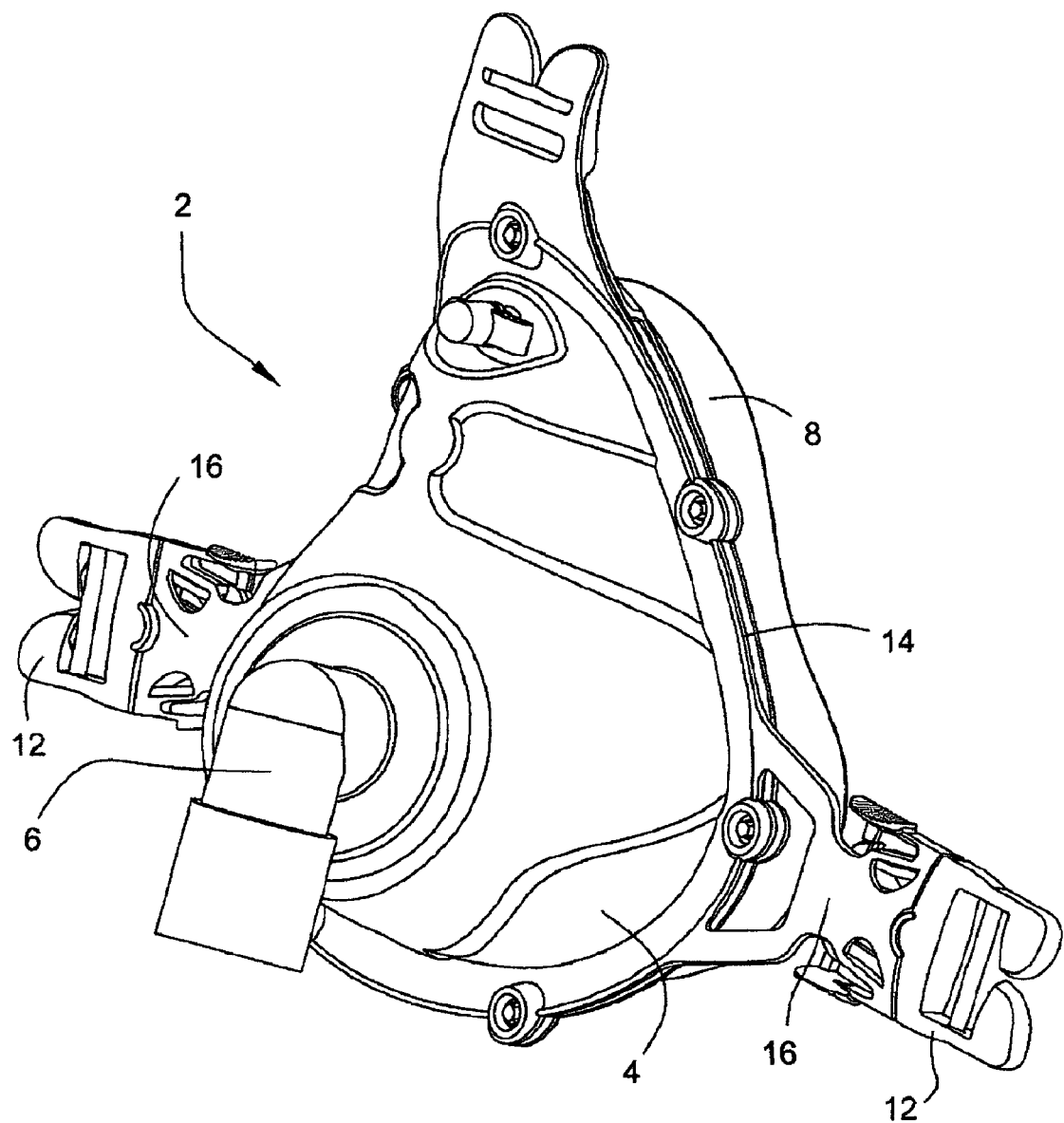
FIG. 1 is a front perspective view of a mask assembly according to an embodiment of the invention.

FIGS. 1 and 6-11 illustrate a mask assembly 2 (also referred to as a mask) for use as part of a ventilation respiratory system according to an embodiment of the present invention.

As illustrated, the mask assembly 2 comprises a frame 4, a swivel connector in the form of an elbow 6 provided to the frame and adapted to be connected to an air delivery tube that delivers breathable gas to the patient, a cushion 8 provided to the frame and adapted to form a seal with the patient's face, a cushion clip 10, and headgear clips 12. The elbow 6 is rotationally mounted to the frame 4 such that it can rotate with a low level of friction. The cushion 8 is attached to the frame 4 via the cushion clip 10 by the clamping of a rim 14 of the cushion 8 between frame 4 and cushion clip 10. The frame 4 comprises clip receptacles 16 and the headgear clips 12 are configured to selectively engage and disengage with respective clip receptacles 16. In use, the headgear clips 12 are attached to headgear adapted to maintain the mask assembly in a desired position on the patient's face.

Figure 2:
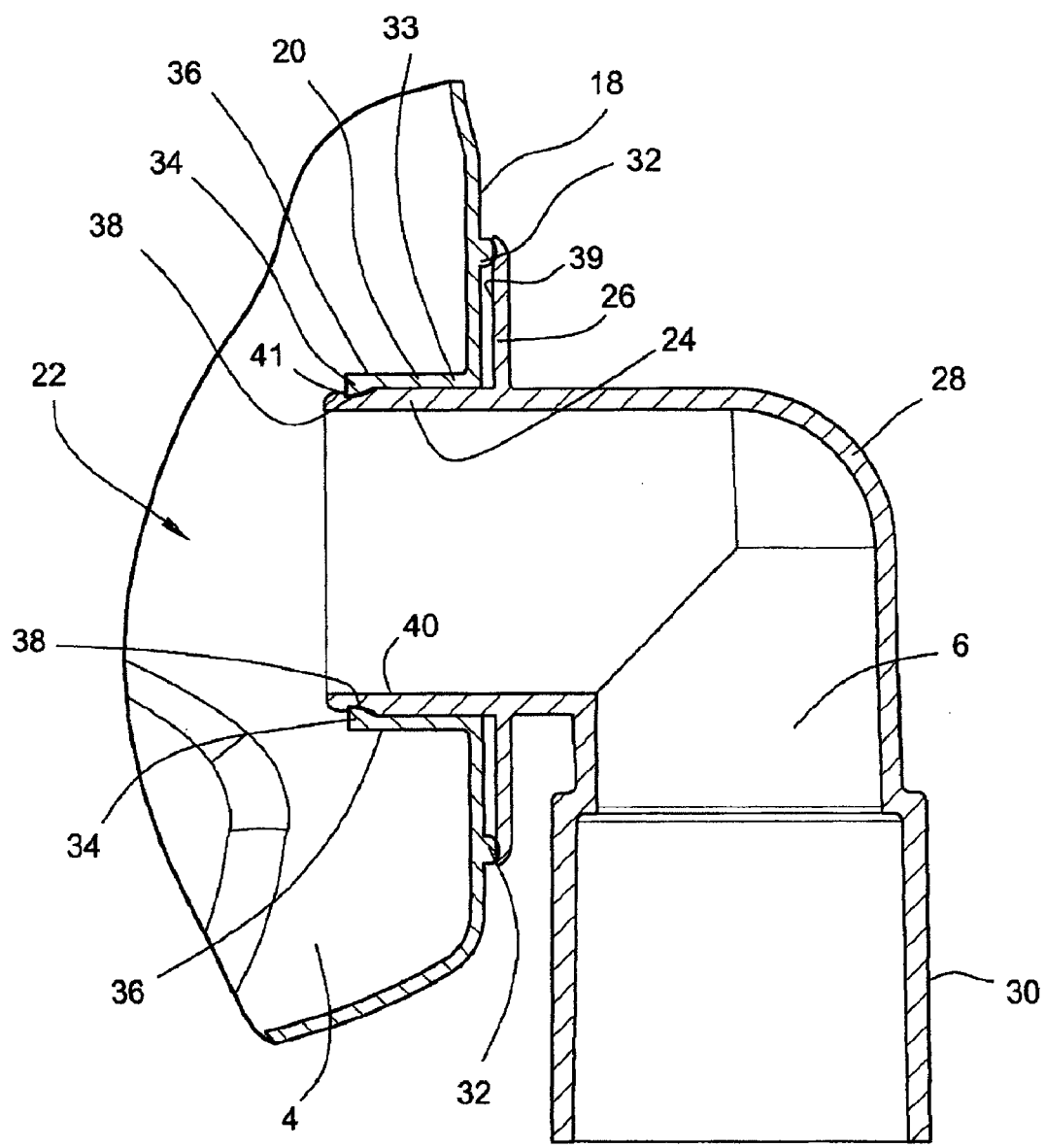
FIG. 2 is a cross-sectional view of a portion of a frame and an elbow of the mask assembly of FIG. 1.

FIG. 2 depicts the elbow 6 engaged in the frame 4. The frame 4 comprises a front surface 18 and an open-ended tube portion 20 protruding from the front surface 18 rearwards into an internal volume 22 of the frame 4. The elbow 6 comprises a tubular insertion portion 24, a circumferential flange 26, a bend 28, and an air tube attachment portion 30.

The external diameter of the insertion portion 24 is slightly smaller than the internal diameter of the tube portion 20 such that the insertion portion 24 can be snugly received in the tube portion 20. The front surface 18 of the frame 4 comprises a plurality of preload ribs 32 (e.g., arcuate ribs or dimples) that surround an outer end 33 of the tube portion 20.

The tube portion 20 comprises an inwardly facing circumferential rib 34 at an inner end 36. The rib 34 is adapted to sealingly interlock or engage a circumferential groove 38 provided on an outer surface of a proximal end 40 of the insertion portion 24 of the elbow 6. This interlocking is made possible by virtue of the geometry of the frame 4, and in particular the fact that the distance between the inner end 36 of the tube portion 20 and the extremity of the preload ribs 32 when the frame 4 is not flexed is greater than the distance between an inside surface 39 of the flange 26 and an engagement surface 41 of the groove 38.

Figure 3:
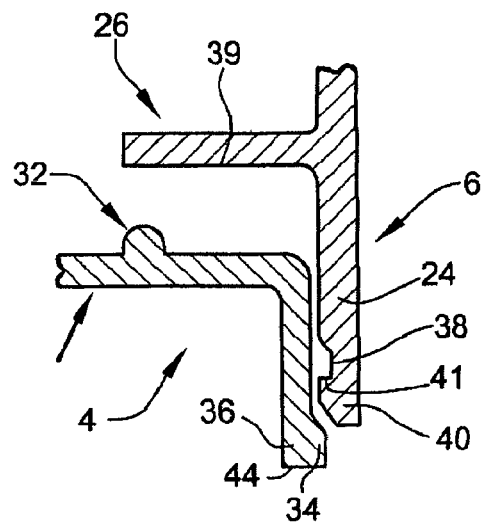
FIG. 3 is an enlarged, schematic cross-sectional view of a portion of a frame and elbow of the mask assembly of FIG. 1, wherein an end of the elbow is being inserted into the frame.
Figure 4:
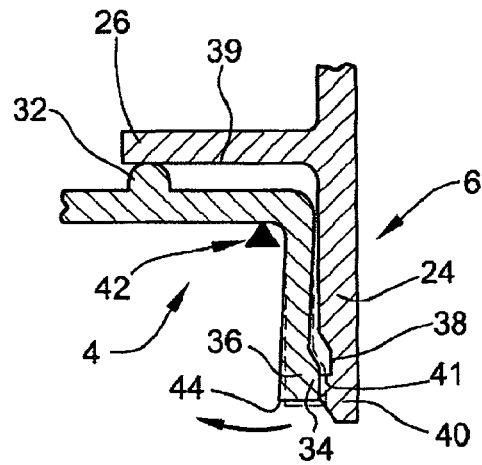
FIG. 4 is an enlarged, schematic cross-sectional view of a portion of a frame and an elbow of the mask assembly of FIG. 1, wherein the elbow is almost engaged in the frame.
Figure 5:
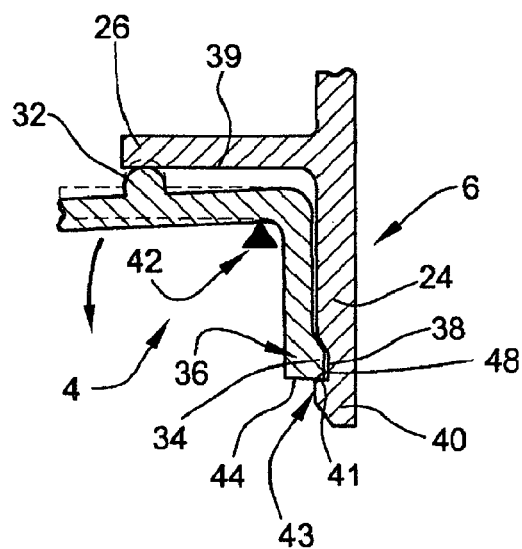
FIG. 5 is an enlarged, schematic cross-sectional view of a portion of a frame and elbow of the mask assembly of FIG. 1, wherein the elbow is engaged in the frame forming a seal against the frame.
Figure 6:
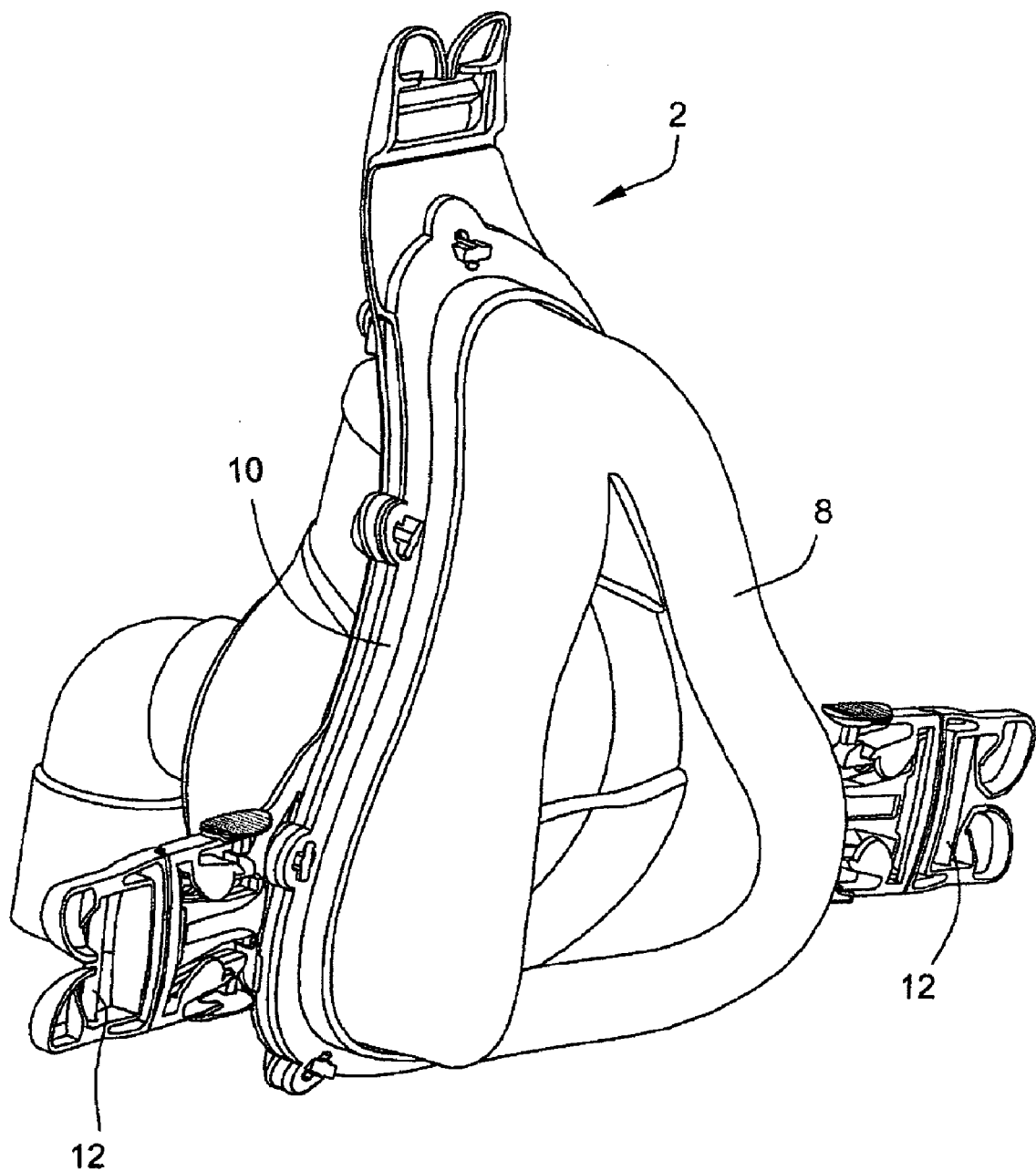
FIG. 6 is a rear perspective view of the mask assembly of FIG. 1.
Figure 7:
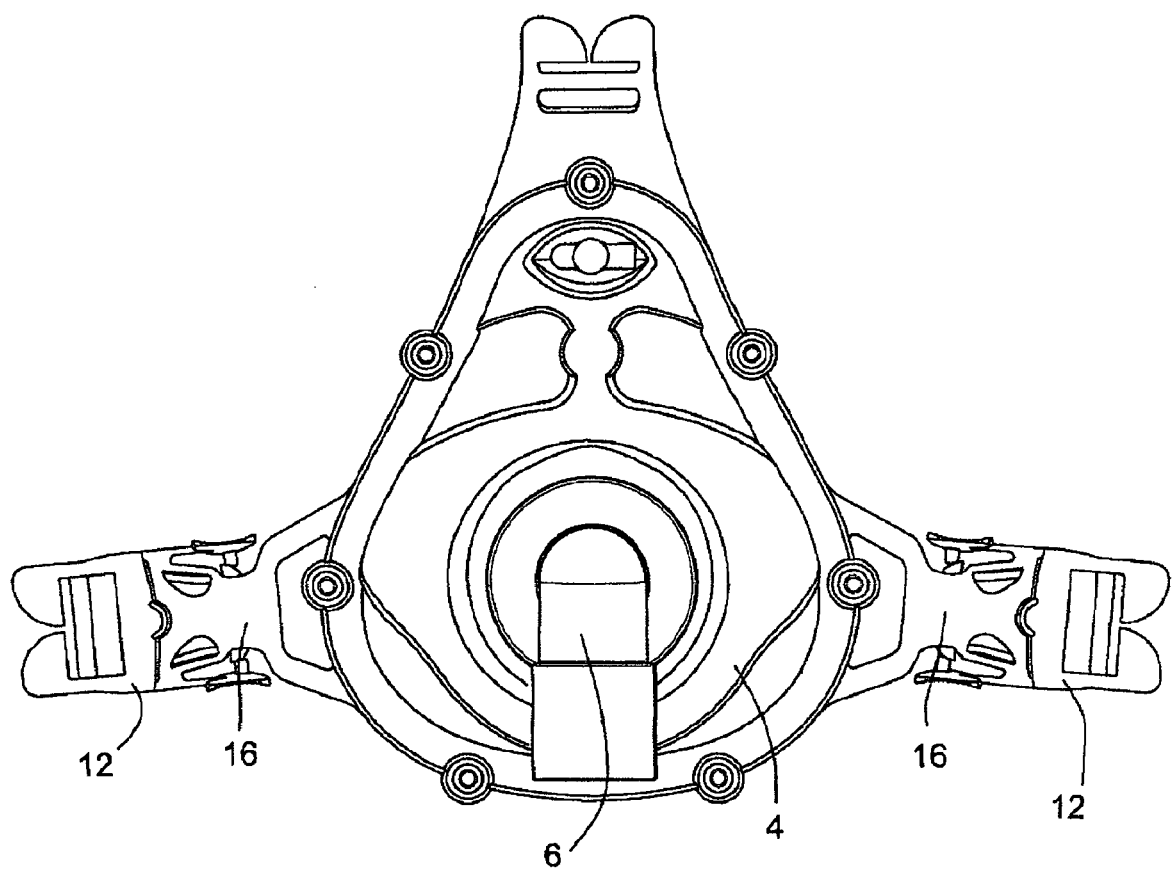
FIG. 7 is a front view of the mask assembly of FIG. 1.
Figure 8:
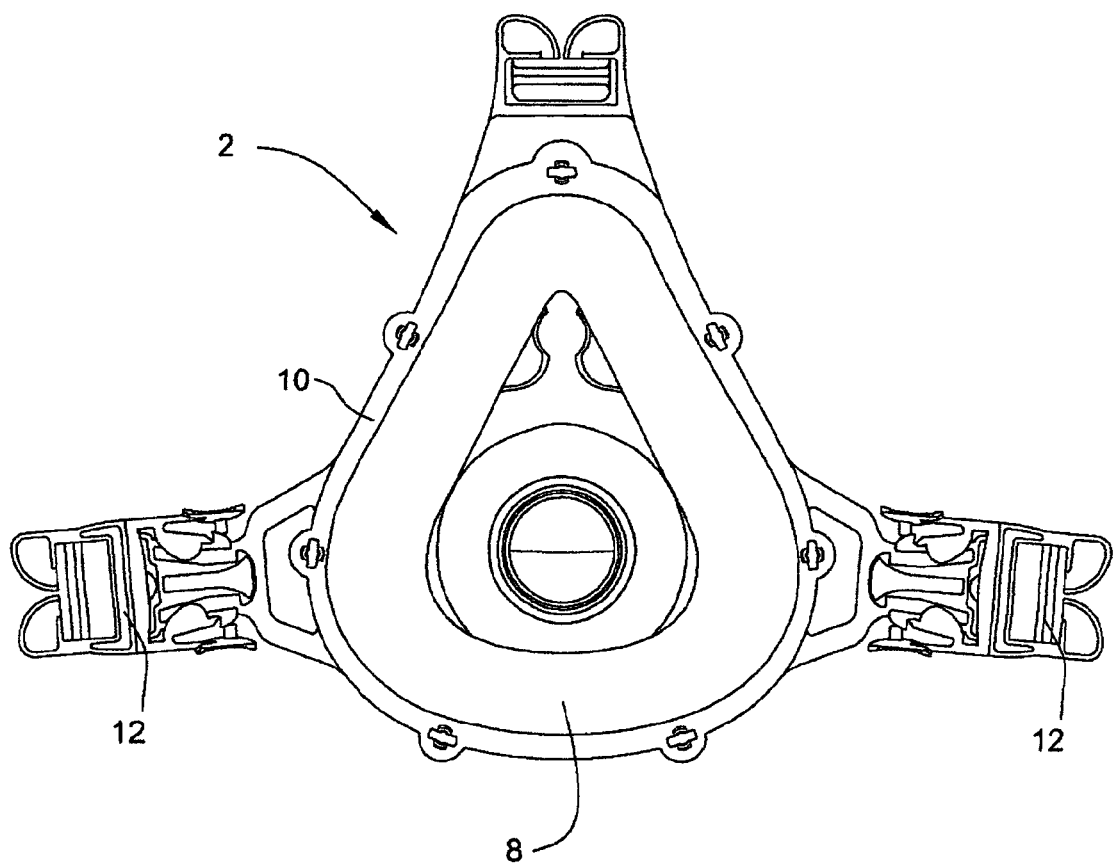
FIG. 8 is a rear view of the mask assembly of FIG. 1.
Figure 9:
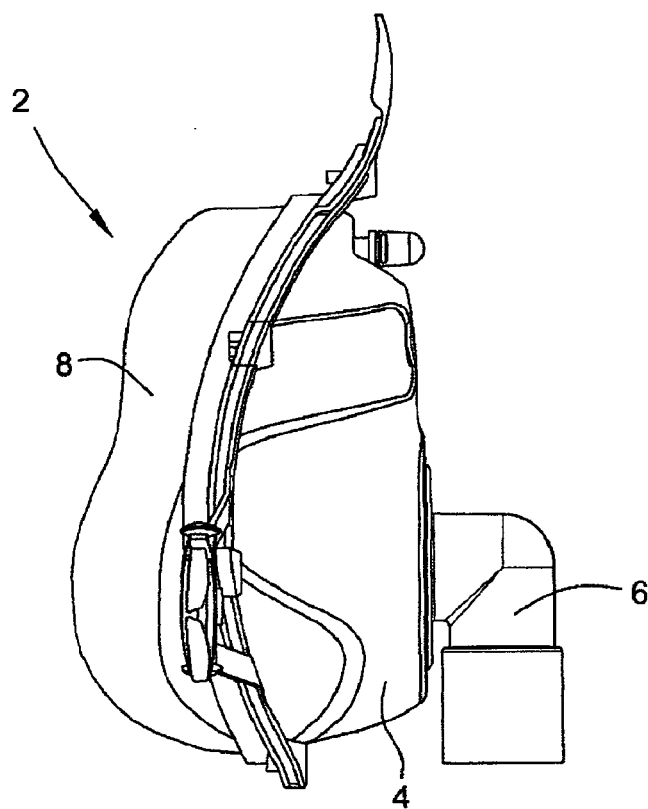
FIG. 9 is a left side view of the mask assembly of FIG. 1.
Figure 10:
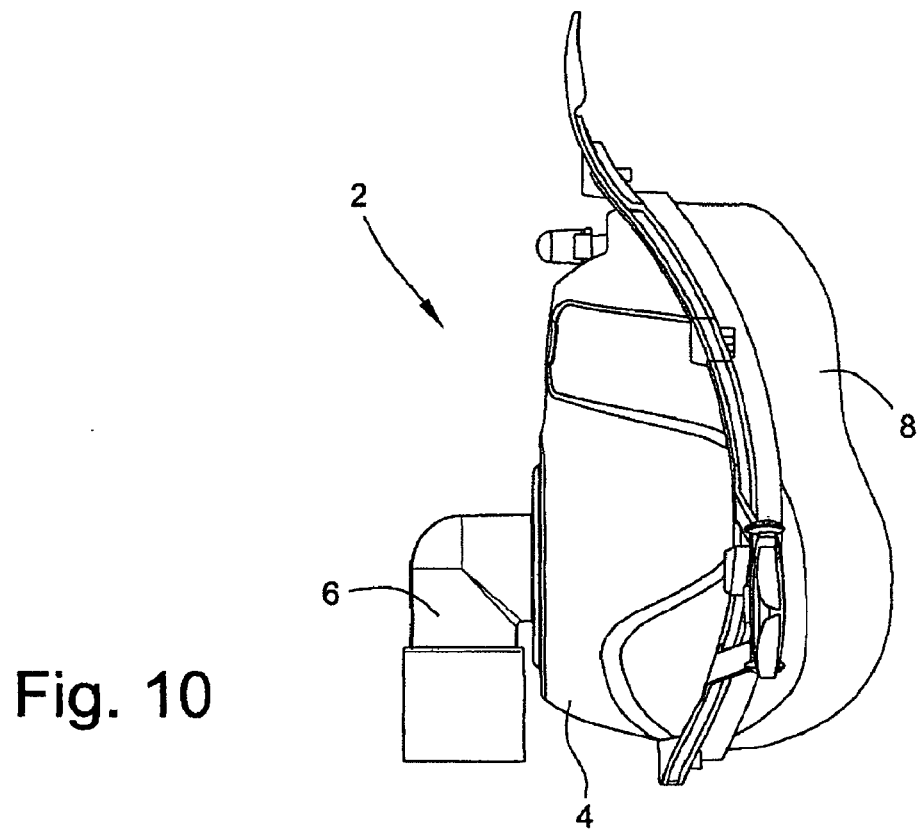
FIG. 10 is a right side view of the mask assembly of FIG. 1.
Figure 11:
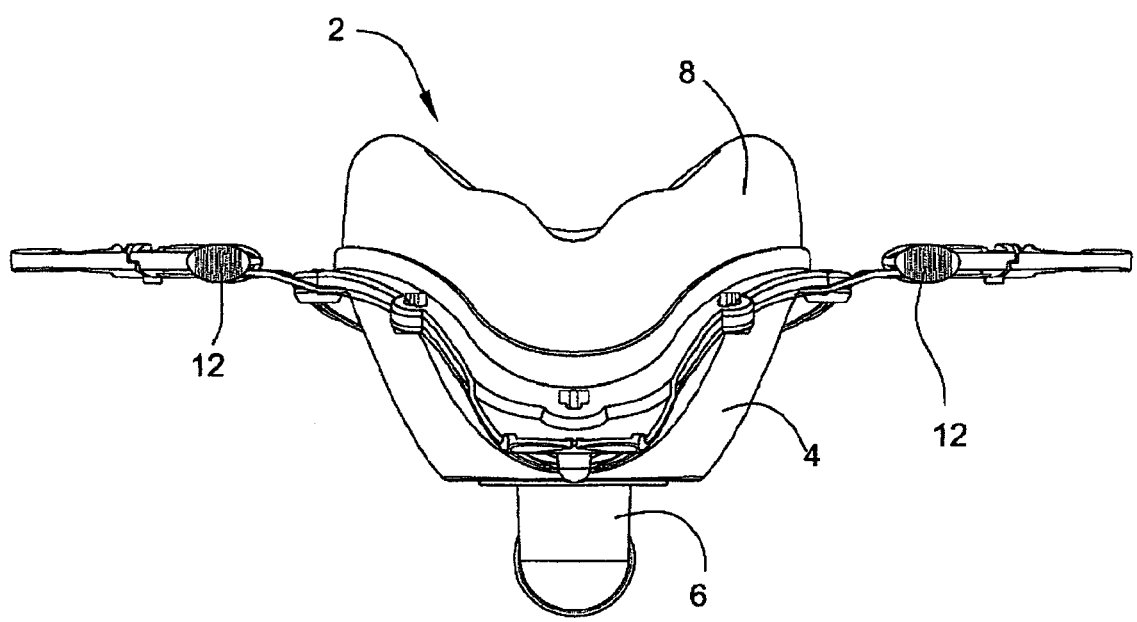
FIG. 11 is a top view of the mask of assembly FIG. 1.
Figure 12:
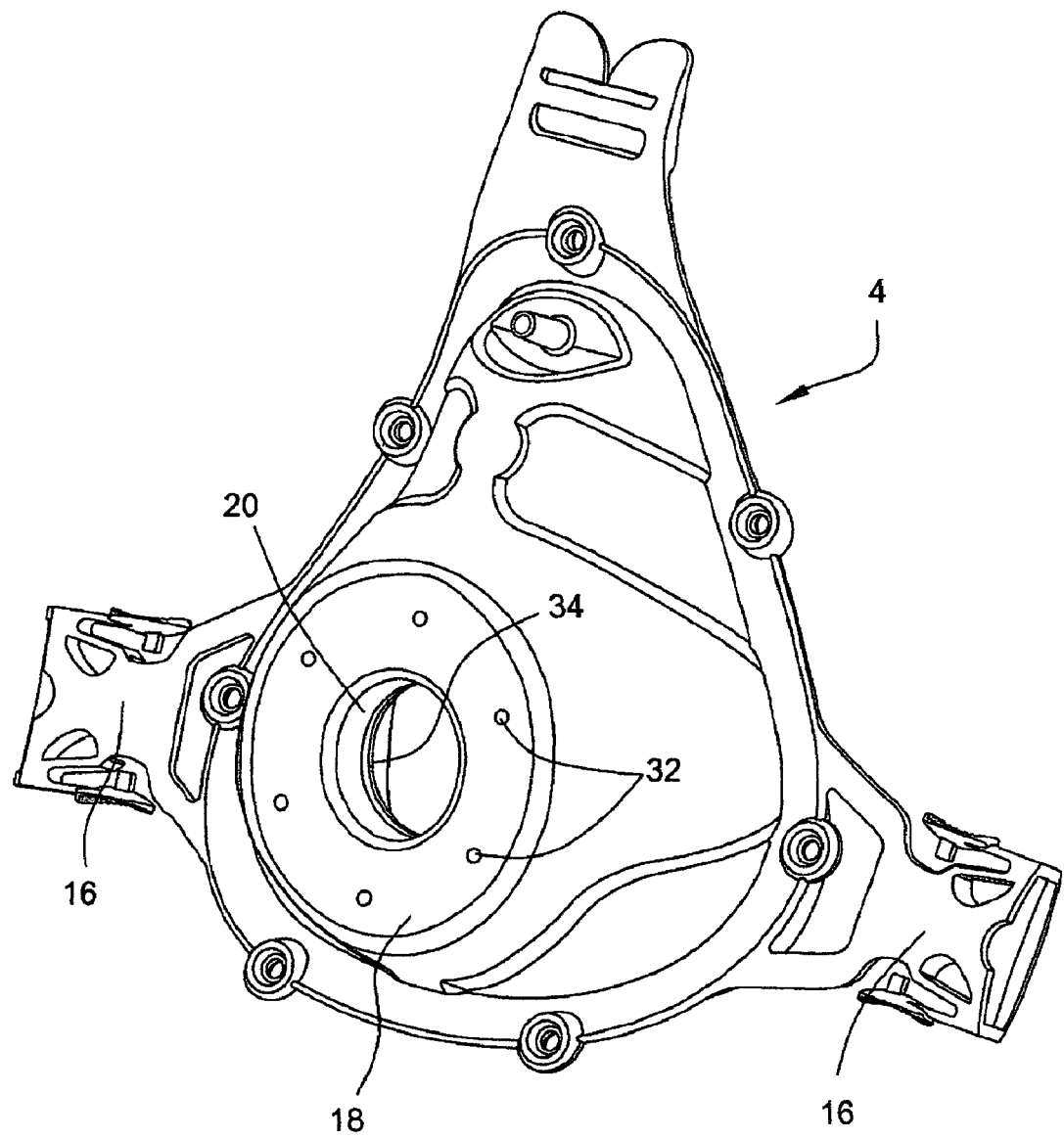
FIG. 12 is a front perspective view of a frame of the mask assembly of FIG. 1.
Figure 13:
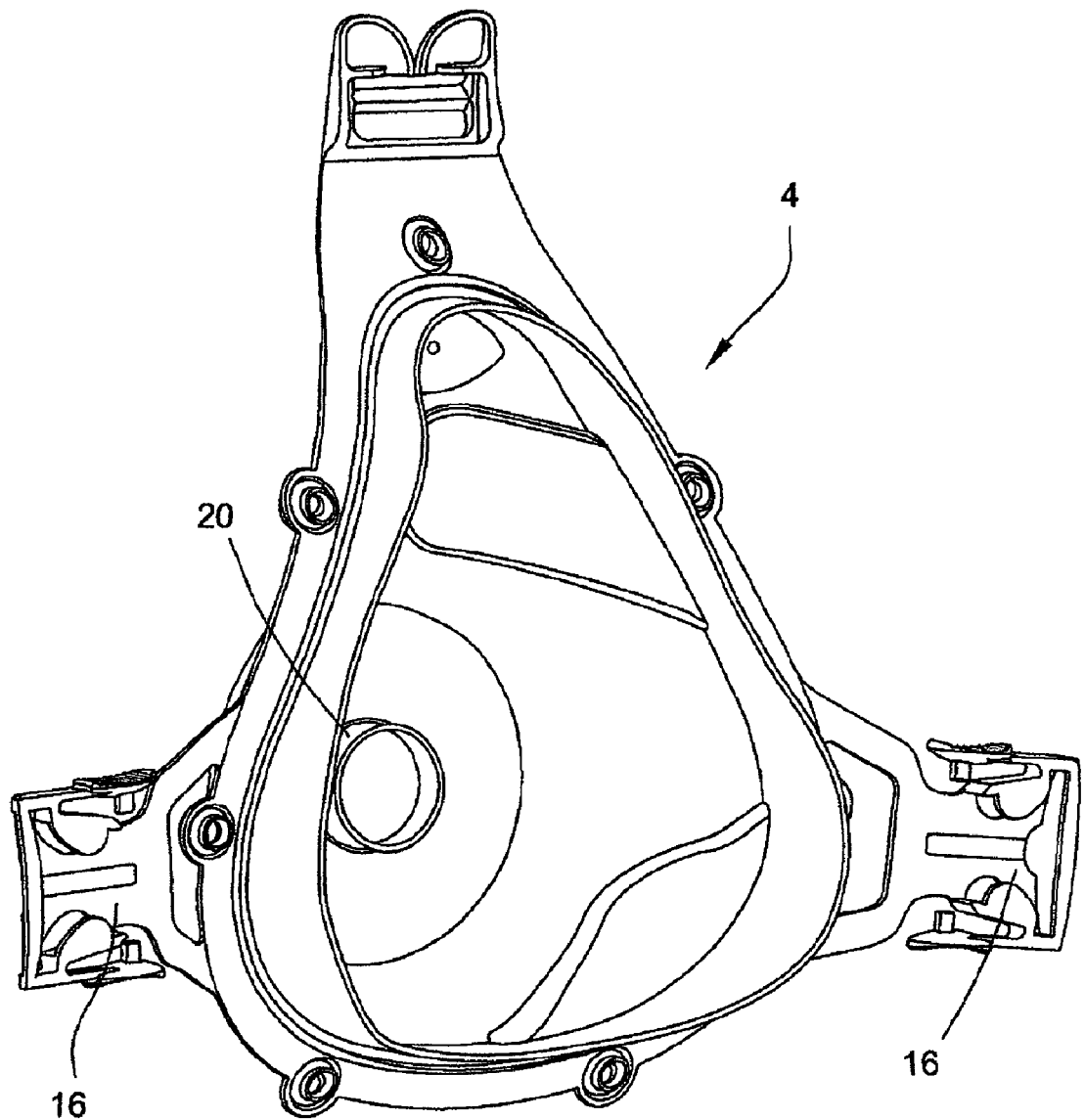
FIG. 13 is a rear perspective view of a frame of the mask assembly of FIG. 1.
Figure 14:
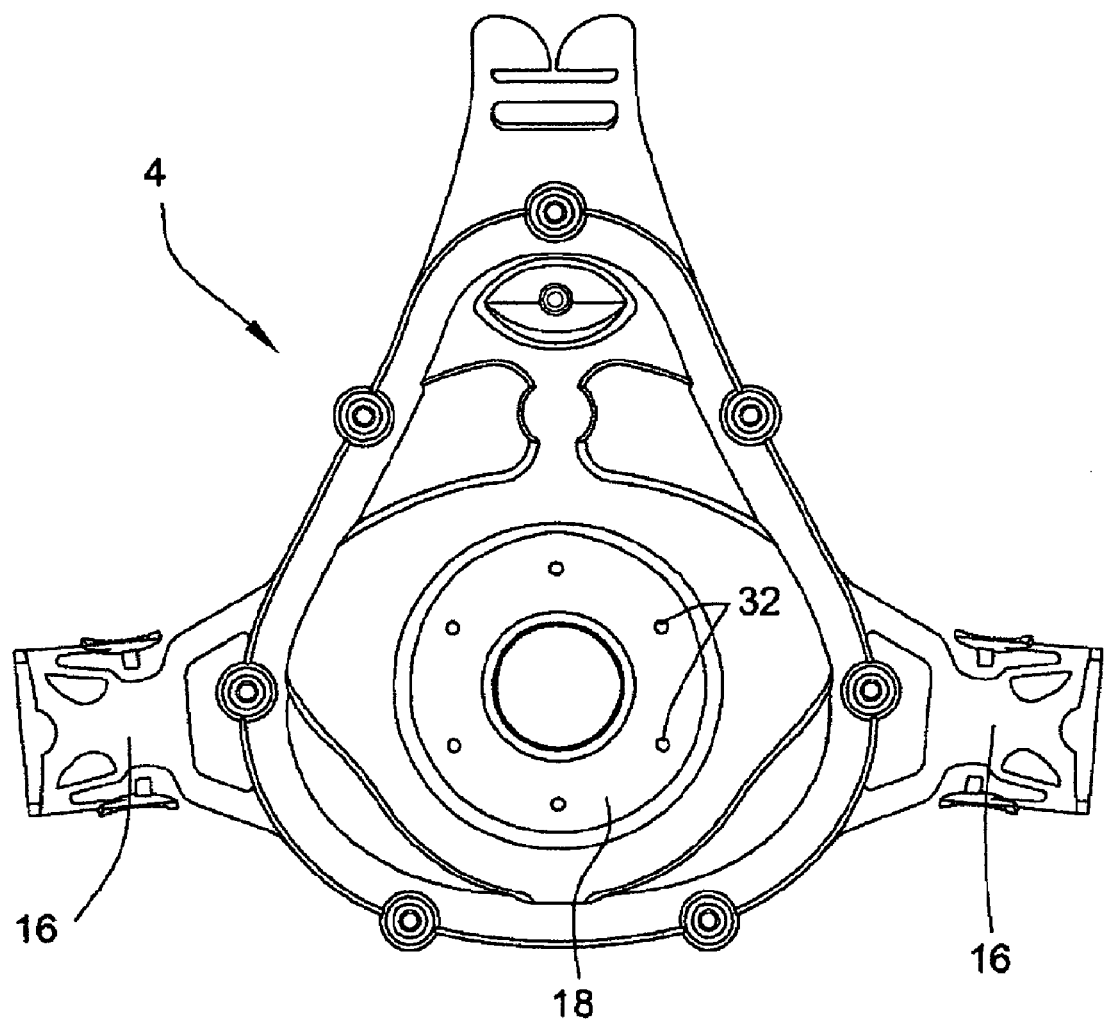
FIG. 14 is a front view of a frame of the mask assembly of FIG. 1.
Figure 15:
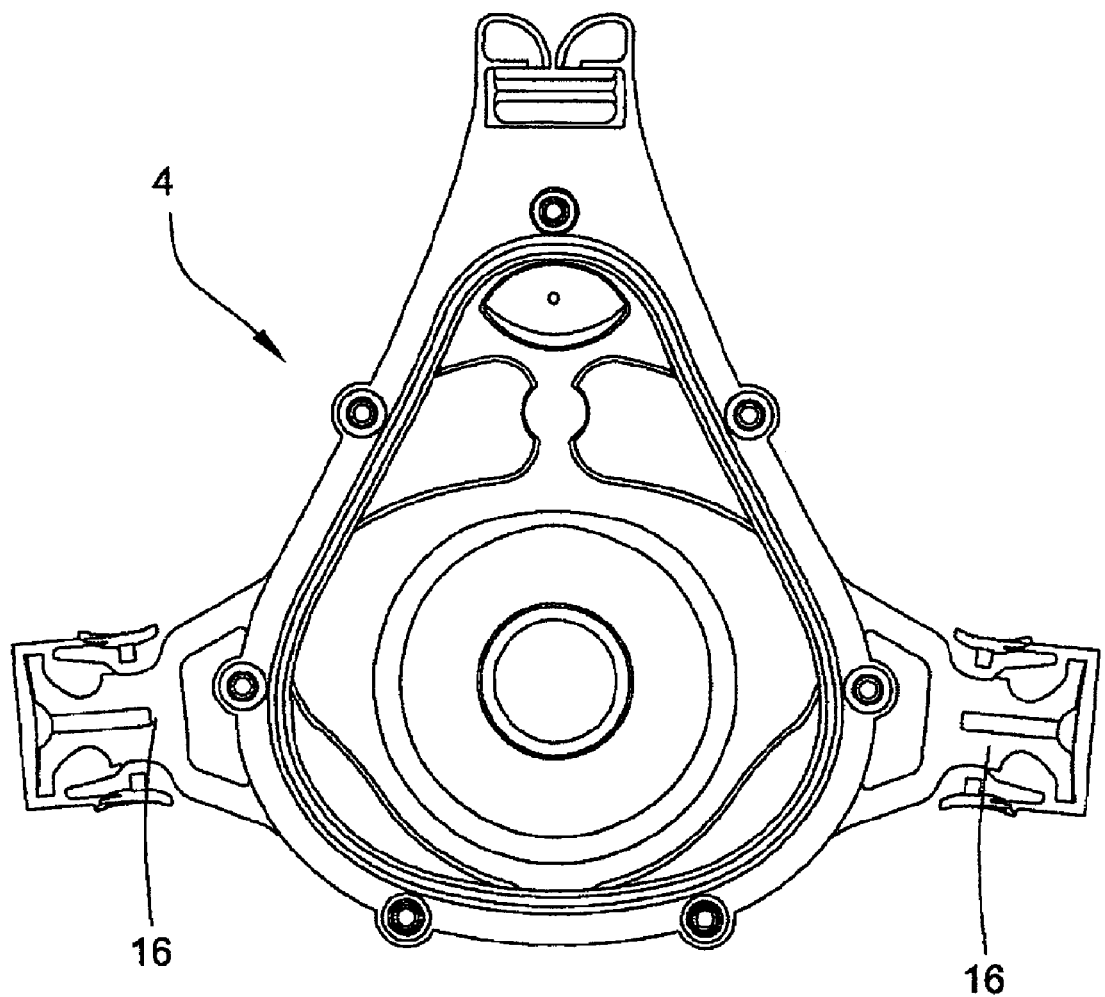
FIG. 15 is a rear view of a frame of the mask assembly of FIG. 1.
Figure 16:
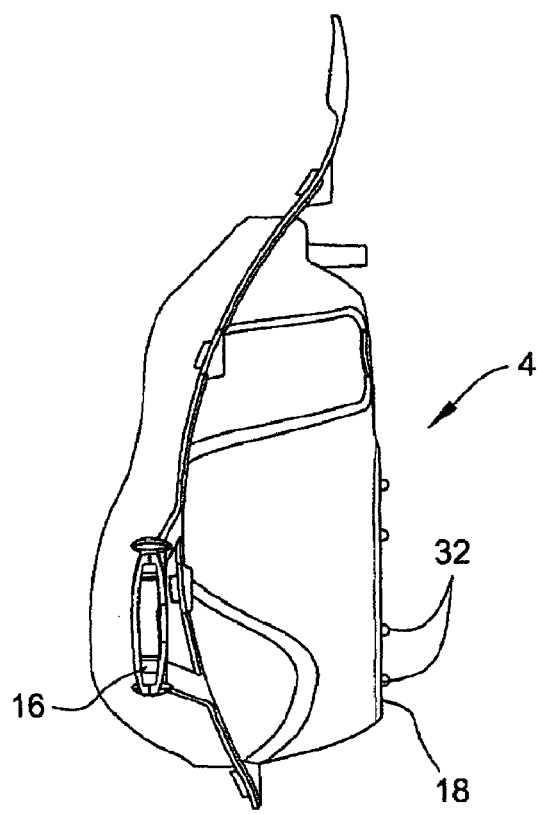
FIG. 16 is a left side view of a frame of the mask assembly of FIG. 1.
Figure 17:
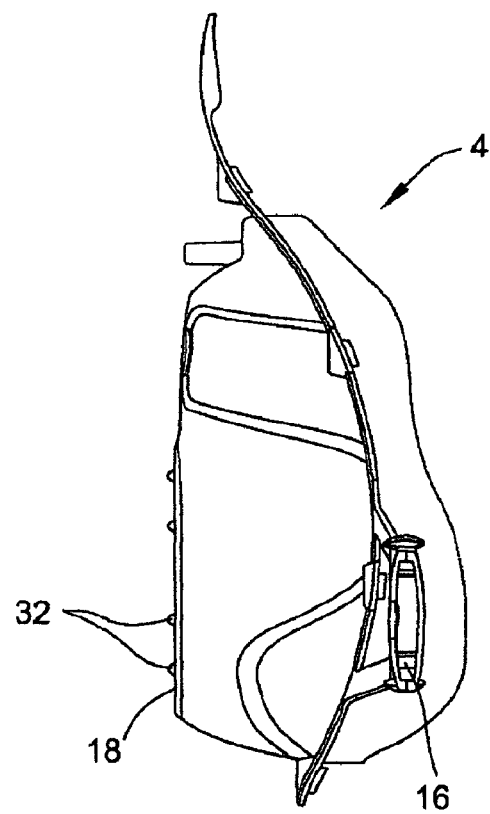
FIG. 17 is a right side view of a frame of the mask assembly of FIG. 1.
Figure 18:
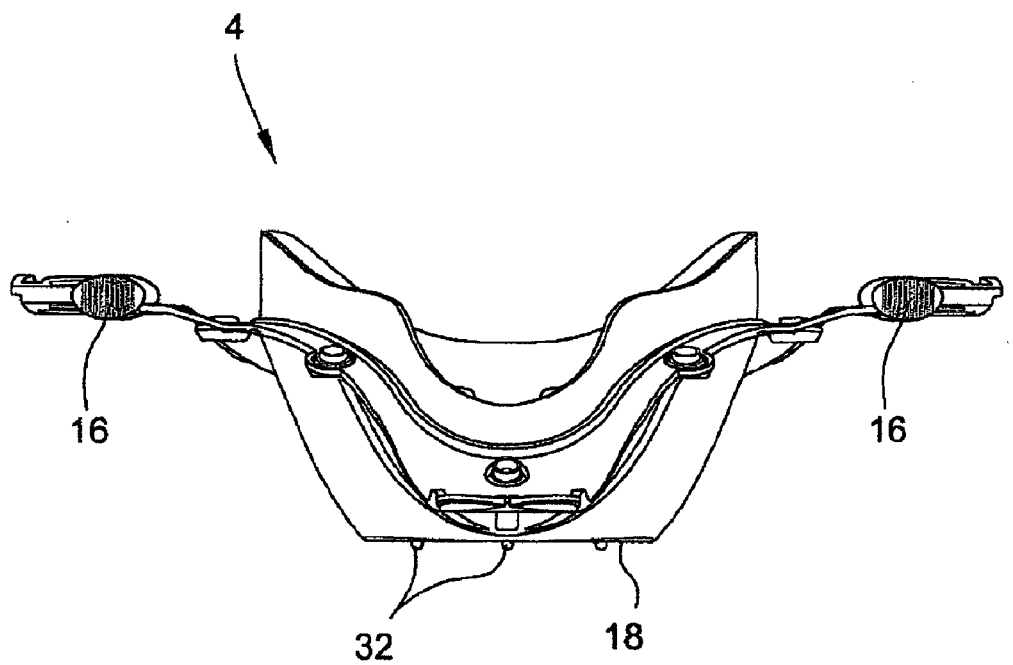
FIG. 18 is a top view of a frame of the mask assembly of FIG. 1.
Figure 19:
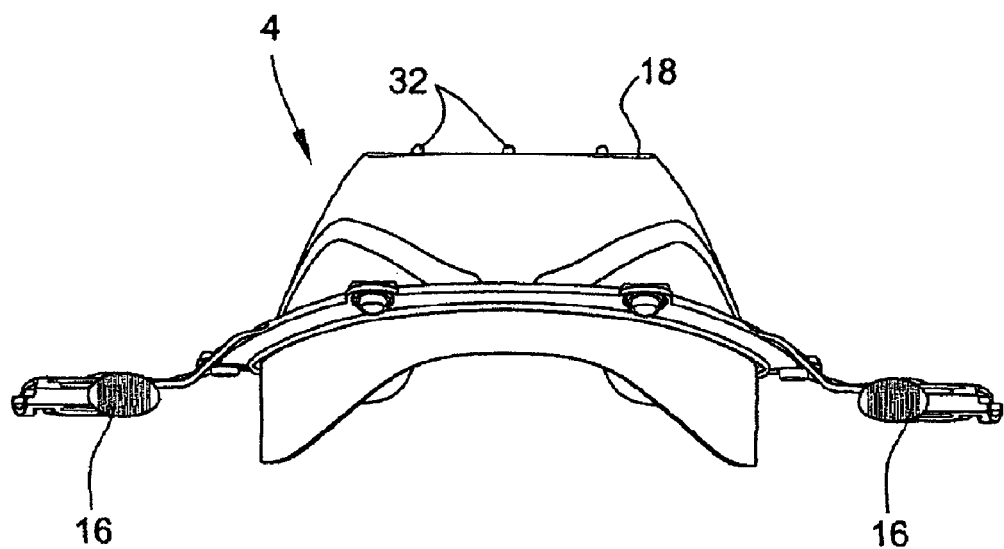
FIG. 19 is a bottom view of a frame of the mask assembly of FIG. 1.
Figure 20:
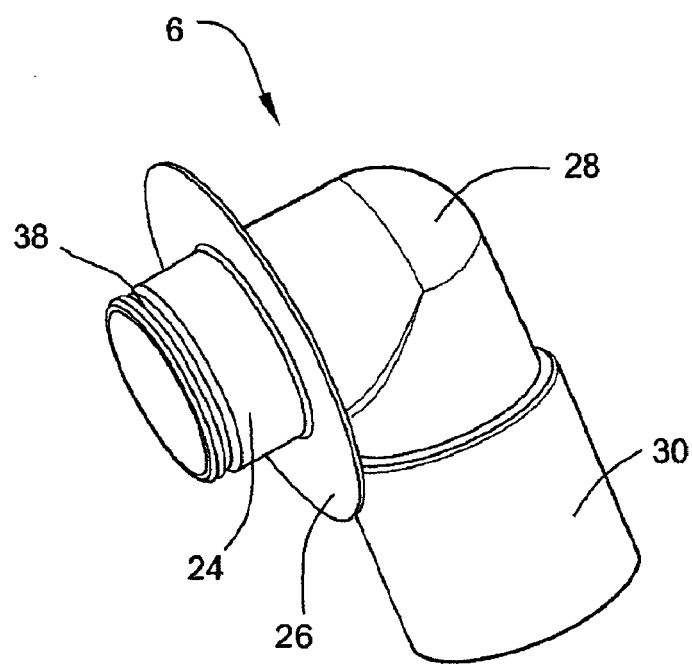
FIG. 20 is a front perspective view of an elbow of the mask assembly of FIG. 1.
Figure 21:
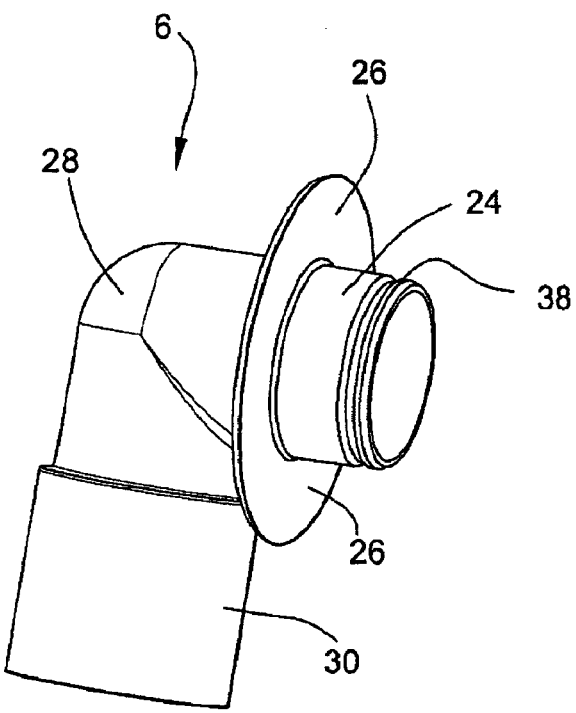
FIG. 21 is a rear perspective view of an elbow of the mask assembly of FIG. 1.
Figure 22:
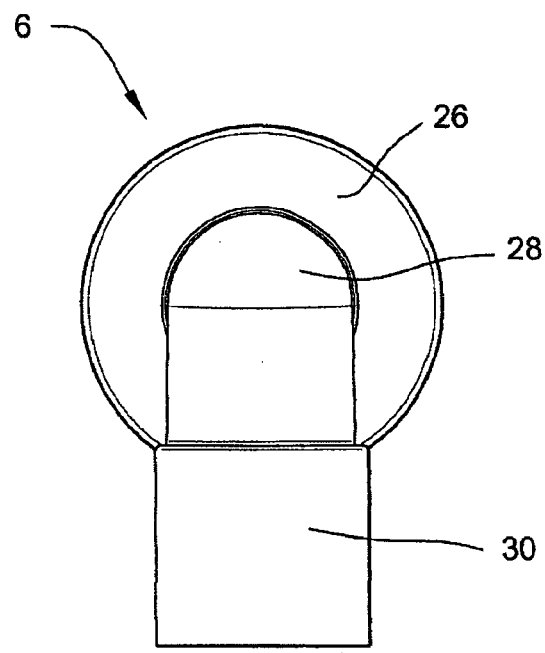
FIG. 22 is a front view of an elbow of the mask assembly of FIG. 1.
Figure 23:
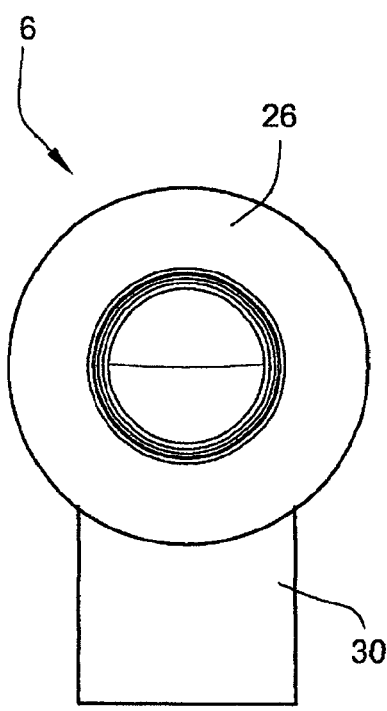
FIG. 23 is a rear view of an elbow of the mask assembly of FIG. 1.
Figure 24:
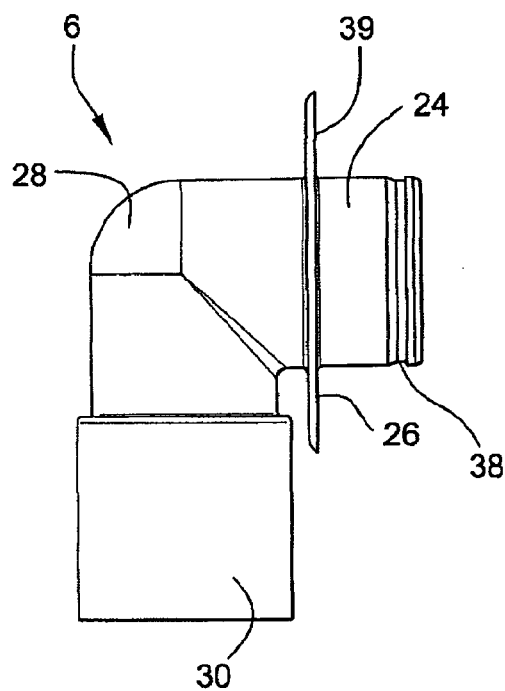
FIG. 24 is a left side view of an elbow of the mask assembly of FIG. 1.
Figure 25:
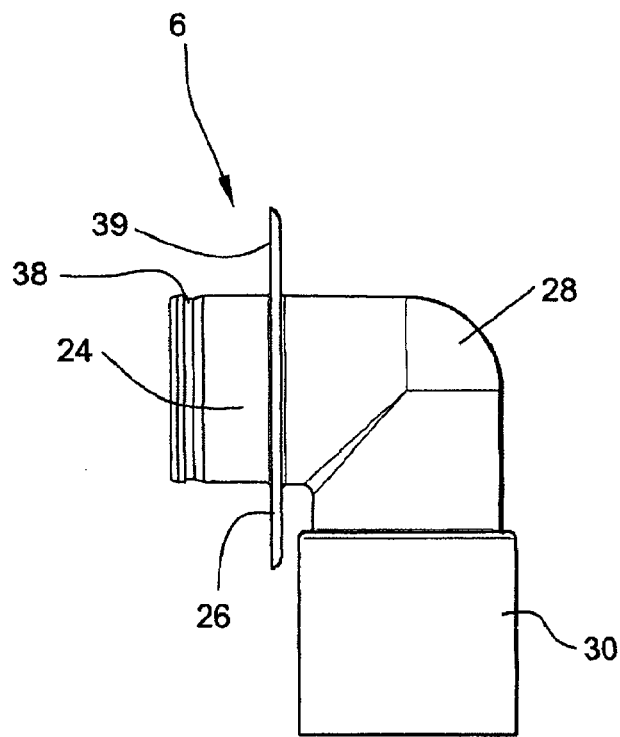
FIG. 25 is a right side view of an elbow of the mask assembly of FIG. 1.
Figure 26:
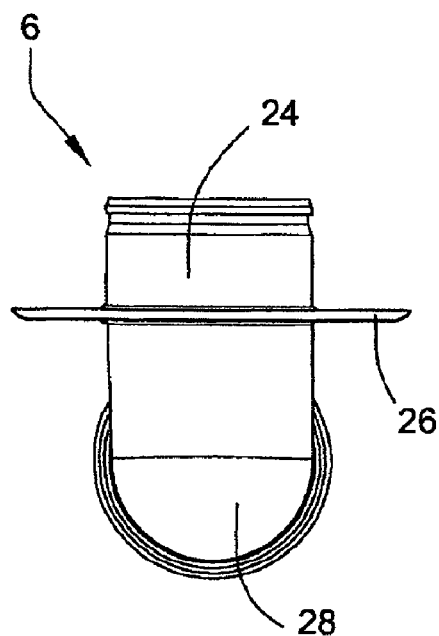
FIG. 26 is a top view of an elbow of the mask assembly of FIG. 1.
Figure 27:
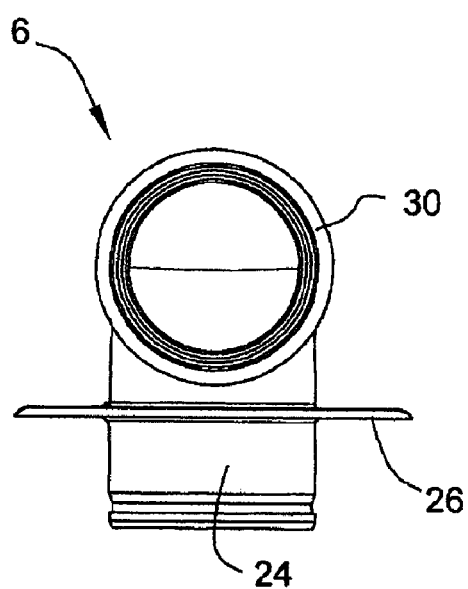
FIG. 27 is a bottom view of an elbow of the mask assembly of FIG. 1.

The process of engaging the elbow 6 and frame 4 will now be described with reference to FIGS. 3 to 5. In FIG. 3, the elbow 6 is being moved towards the frame 4 and the inside surface 39 of the circumferential flange 26 is yet to engage the preload ribs 32. In FIG. 4, the inside surface 39 has come into contact with the preload ribs 32. As a load 42 (shown in FIG. 4) is applied, the inner end 36 of the tube portion 20 deforms (from the portion indicated in dashed lines to the portion indicated in solid lines). In FIG. 5, the deformation has occurred to the extent that the rib 34 has engaged with the groove 38 to form an annular sealing area 43. The distance between the inner end 36 of the tube portion 20 and the extremity of the preload ribs 32 when the frame 4 is not flexed is greater than the distance between an inside surface 39 of the flange 26 and an engagement surface 41 of the groove 38. Consequently, the frame 4 resiliently flexes biasing the rib 34 into the groove 38 to maintain the seal.

As can be seen in FIG. 5, when the rib 34 is engaged with the groove 38, the annular sealing area 43 is formed between an end surface 44 of the open-ended tube portion 20 and the engagement surface 41 of the tubular insertion portion 24. The rib 34 snap-locks into the groove 38 and provides a sound that indicates that a seal has formed. In an alternative embodiment, a generally annular sealing line may be formed between the preload ribs 32 and the inside surface 39 of the flange 26. In yet another embodiment, both seals are provided.

In the illustrated embodiment, each preload rib 32 has a semi-circular cross-section which is advantageous in that the line of sealing rolls smoothly along the inside surface 39 of the flange 26 as the frame 4 flexes. In an alternative embodiment, each preload rib 32 may have a flat top and radiused corners such that it has a substantially trapezoidal, rectangular or square cross-section. This arrangement provides a larger contact area to reduce the contact pressure, resulting in the elbow being more smoothly rotatable. It should be appreciated that each preload rib 32 could have any other suitable cross-section. In the illustrated embodiment, the rib 34 has a trapezoidal cross-section, wherein an inner surface 48 thereof forms part of the annular sealing area 43.

As best shown in FIGS. 12, 14, and 16-19, the front surface 18 of the frame 4 is a relatively flat and annular-shaped, and the plurality of preload ribs or dimples 32 extend forwardly from the front surface 18. In the illustrated embodiment, six preload ribs 32 are regularly separated and spaced from another along an arc or circle on the front surface 18 of the frame 4. However, the frame 4 may include any suitable number of preload ribs 32, e.g., at least one rib, less than six preload ribs, more than six preload ribs, etc. In addition, the preload ribs 32 may be provided to the front surface 18 in other suitable arrangements, e.g., ribs arranged in concentric circles, random spacing, etc. In an alternative embodiment, the preload rib may be in the form of a continuous, circumferential preload rib.

In an alternative embodiment, the inner end 36 of the tube portion 20 may be replaced by a number of fingers having grooves on their finger tips that interlock with the rib 34.

It should be appreciated that the term "seal" also refers to effective degrees of sealing where there is a relatively small amount of leak. For example, a leak of between 0.1 and 5.9 L/min. For another example, a leak of between 0.5 and 1.5 L/min. For another example, a leak of about 1 L/min.

In the illustrated embodiment, the frame 4 is made of polypropylene. It has been found that this material is difficult to mold to precise dimensions. This results in loose tolerances making it difficult to form an effective seal between components. Advantageously, the mask assembly 2 is structured to provide an effective seal between the frame 4 and the elbow 6 without precise tolerances.

A further advantage of the mask assembly 2 is that it allows the elbow 6 to rotate in the frame 4 with a low level of friction.

Yet another advantage of the mask assembly 2 is that no additional sealing component is required to achieve an effective seal between the frame 4 and elbow 6. This avoids the addition of a sealing component between the elbow 6 and the frame 4 which reduces the cost of goods.

In the illustrated embodiment, the elbow 6 is formed from a Makrolon polycarbonate. Both the frame 4 and elbow 6 may be formed from any other suitable engineering materials such as polystyrene, polymethylmethacrylate, polysulfone, polyethylene or nylon. In an embodiment, the frame 4 may be made from a more flexible material than the elbow 6. In another embodiment, both the frame 4 and elbow 6 may be formed from polypropylene or another relatively soft plastic material.

FIGS. 6-11 show other views of the mask assembly 2 that clarify the geometry and configuration of some of the components described above. FIGS. 12-19 show various views of the frame 4 that clarify the geometry and configuration of some of the portions of the frame described above. FIGS. 20-27 show various views of the elbow 6 that clarify the geometry and configuration of some of the portions of the elbow described above. For example, FIGS. 20-27 clearly show the elbow 6 and its circumferential flange 26 and the groove 38 at the end of the tubular insertion portion 24.

In another embodiment, the mask assembly 2 may include a vent so that it may be used in CPAP or bi-level therapies.

It should also be appreciated that the preload sealing arrangement described above can be used to effect a seal between other mask components, for example between a swivel member and a frame or between a swivel member and an elbow.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. Also, the various embodiments described above may be implemented in conjunction with other embodiments, e.g., aspects of one embodiment may be combined with aspects of another embodiment to realize yet other embodiments. Further, each independent feature or component of any given assembly may constitute an additional embodiment. In addition, while the invention has particular application to patients who suffer from OSA, it is to be appreciated that patients who suffer from other illnesses (e.g., congestive heart failure, diabetes, morbid obesity, stroke, bariatric surgery, etc.) can derive benefit from the above teachings. Moreover, the above teachings have applicability with patients and non-patients alike in non-medical applications.

What is claimed is:

1. A mask assembly for use in providing a supply of air at positive pressure to the airways of a patient, the mask assembly comprising:
a frame and an elbow, the elbow being rotatable with respect to the frame when assembled, the frame including an elbow-receiving portion, the elbow and the elbow-receiving portion of the frame including respective interlocking sealing portions and respective engaging portions spaced from the sealing portions so that, when the respective engaging portions are engaged, one of the elbow and the elbow-receiving portion forms a flexible element that, upon assembly, flexes to introduce a preload that effects a seal between the respective interlocking sealing portions.

2. The assembly of claim 1, wherein the flexible element resides on the elbow-receiving portion of the frame.

3. The assembly of claim 1, wherein the elbow-receiving portion of the frame is constructed from polypropylene.

4. The assembly of claim 1, wherein the elbow is constructed from polycarbonate.

5. A frame for use in a mask assembly used in providing respiratory therapies, the mask assembly being connectable to an air delivery conduit via a swivel connector, the mask assembly having an interior and an exterior, the frame comprising:
a swivel connector-receiving portion, the swivel connector-receiving portion including a flexing portion and an interlocking portion spaced and separated from the flexing portion, the interlocking portion being adapted to engage with a corresponding interlocking portion on the swivel connector and the flexing portion being adapted to flex through contact of the flexing portion with the swivel connector and to thereby induce a seal between the respective interlocking portions to substantially reduce a leak flow of air from a mask assembly interior to a mask assembly exterior between the frame and swivel connector.

6. The frame of claim 5, wherein the swivel connector-receiving portion is a swivel elbow-receiving portion.

7. The frame of claim 5, wherein the flexing portion is constructed from polypropylene.

8. The frame of claim 5, wherein the swivel connector receiving portion is substantially cylindrical portion having an inside diameter, a proximal end, and a distal end.

9. The frame of claim 8, wherein the swivel connector receiving portion includes an interlocking portion near the distal end.

10. The frame of claim 9, wherein the interlocking portion is located on an interior surface of the swivel connector receiving portion.

11. The frame of claim 8, wherein the swivel connector receiving portion defines a length between the proximal end and the interlocking portion.

12. The frame of claim 5, wherein the swivel connector receiving portion is adapted for engagement with a swivel connector having a substantially cylindrical portion having an external diameter and a length.

13. The frame of claim 5, wherein the inside diameter of the substantially cylindrical portion of the frame is substantially larger than the external diameter of the substantially cylindrical portion of the swivel connector.

14. The frame of claim 5, wherein the length of the cylindrical portion of the swivel connector-receiving portion of the frame is less than the length of the cylindrical portion of the swivel connector.

15. A connector adapted to sealingly and swivelingly interconnect an air delivery conduit and a frame of a mask assembly for use in non-invasive ventilation, the connector comprising:
a first end for interconnection with the air delivery conduit; and
a second end for interconnection with the frame, the second end having an interlocking portion adapted to swivelingly engage with a corresponding interlocking portion of the frame, the second end including an engaging portion spaced from the interlocking portions so that, through engagement of the engaging portion with a flexing portion of the frame, the interlocking portion of the second end sealingly engages the interlocking portion of the frame.

16. The connector of claim 15, wherein the connector is a swivel elbow.

17. The connector of claim 15, wherein the connector is constructed from polycarbonate.

18. An assembly comprising a frame as claimed in claim 5 and a connector.

19. An assembly for use in non-invasive ventilation, comprising:
a connector as claimed in claim 15; and
a frame connected to the connector.

20. The assembly of claim 1, wherein the engaging portion of the frame includes a plurality of ribs, and the engaging portion of the elbow includes a flange.

21. The frame of claim 5, wherein the flexing portion includes a plurality of ribs to contact the swivel connector.

22. The connector of claim 15, wherein the engaging portion of the connector includes a flange.

* * * * *